United States Patent
Lange et al.

(10) Patent No.: US 11,103,512 B2
(45) Date of Patent: *Aug. 31, 2021

(54) CRYSTALLINE FORM OF (S)-[2-CHLORO-4-FLUORO-5-(7-MORPHOLIN-4-YL-QUINAZOLIN-4-YL)PHENYL]-(6-METHOXY-PYRIDAZIN-3-YL)-METHANOL

(71) Applicant: Merck Patent GmbH, Darmstadt (DE)

(72) Inventors: Michael Lange, Darmstadt (DE); Clemens Kuehn, Darmstadt (DE); Thomas Fuchss, Bensheim-Auerbach (DE); David Maillard, Darmstadt (DE); Marcel Breuning, Frankfurt am Main (DE); Marco Poma, Rome (IT); Edoardo Burini, Guidonia Montecelio (IT)

(73) Assignee: Merck Patent GmbH, Darmstadt (DE)

(*) Notice: Subject to any disclaimer, the term of this patent is extended or adjusted under 35 U.S.C. 154(b) by 79 days.

This patent is subject to a terminal disclaimer.

(21) Appl. No.: 16/498,873

(22) PCT Filed: Mar. 28, 2018

(86) PCT No.: PCT/EP2018/057869
§ 371 (c)(1),
(2) Date: Sep. 27, 2019

(87) PCT Pub. No.: WO2018/178129
PCT Pub. Date: Oct. 4, 2018

(65) Prior Publication Data
US 2021/0113572 A1    Apr. 22, 2021

(30) Foreign Application Priority Data

Mar. 30, 2017   (EP) ..................... 17163821

(51) Int. Cl.
A61K 31/5375 (2006.01)
C07D 413/00 (2006.01)
A61P 35/00 (2006.01)
A61K 31/5377 (2006.01)
A61K 45/06 (2006.01)
A61N 5/10 (2006.01)
C07D 403/10 (2006.01)

(52) U.S. Cl.
CPC .......... *A61K 31/5377* (2013.01); *A61K 45/06* (2013.01); *A61N 5/10* (2013.01); *C07D 403/10* (2013.01); *C07B 2200/13* (2013.01)

(58) Field of Classification Search
CPC .... A61K 31/5375; C07D 413/00; A61P 35/00
USPC ........................................ 514/232.8; 544/116
See application file for complete search history.

(56) References Cited

U.S. PATENT DOCUMENTS

| | | | |
|---|---|---|---|
| 9,732,094 | B2 | 8/2017 | Fuchss et al. |
| 10,172,859 | B2 | 1/2019 | Fuchss et al. |
| 10,383,874 | B2 | 8/2019 | Fuchss et al. |
| 2016/0083401 | A1 | 3/2016 | Fuchss et al. |
| 2017/0290836 | A1 | 10/2017 | Fuchss et al. |
| 2019/0142833 | A1 | 5/2019 | Fuchss et al. |

FOREIGN PATENT DOCUMENTS

WO    2014/183850    11/2014

OTHER PUBLICATIONS

International Search Report dated May 11, 2018 in PCT/EP2018/057869.
Written Opinion dated May 11, 2018 in PCT/EP2018/057869.
Smith et al., "The DNA-dependent protein kinase," Genes & Development 13:916-934, 1999.
Office Action dated Jul. 9, 2021 in U.S. Appl. No. 16/498,943.

*Primary Examiner* — Raymond J Henley, III
(74) *Attorney, Agent, or Firm* — Grüneberg and Myers PLLC

(57) ABSTRACT

A crystalline form of (S)-[2-chloro-4-fluoro-5-(7-morpholin-4-yl-quinazolin-4-yl)-phenyl]-(6-methoxy-pyridazin-3-yl)-methanol can be prepared as a pharmaceutical composition.

19 Claims, 7 Drawing Sheets

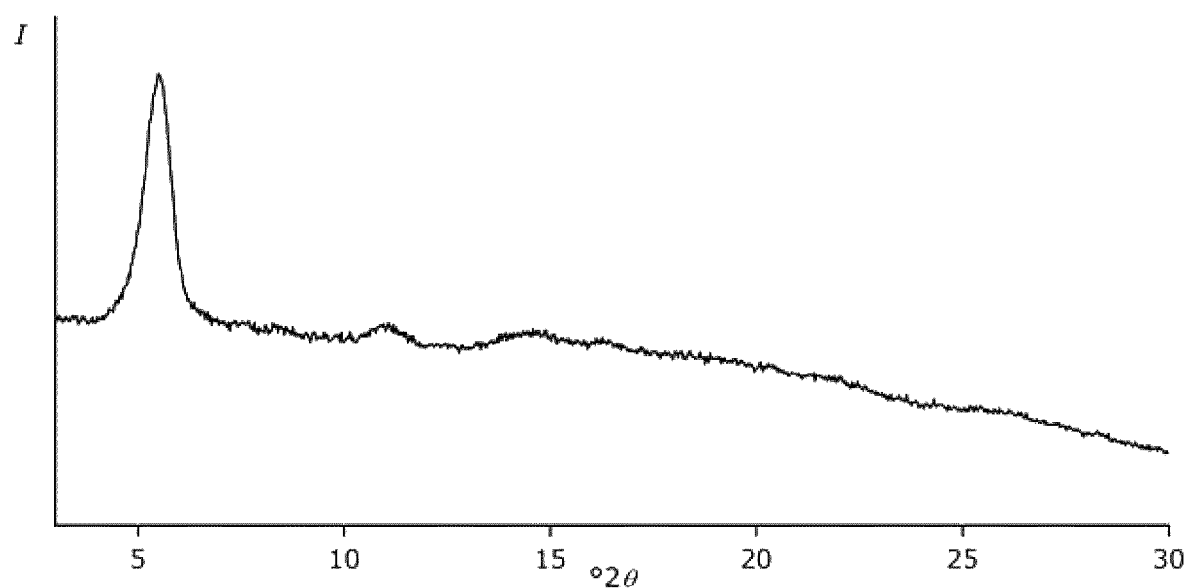
Figure 1: Powder X-ray diffractogram of amorphous form

DSC scan of amorphous material: reversing heat flow

DSC scan of amorphous material: non-reversing heat flow

Water Vapour Sorption Isotherm (25 °C) of amorphous material

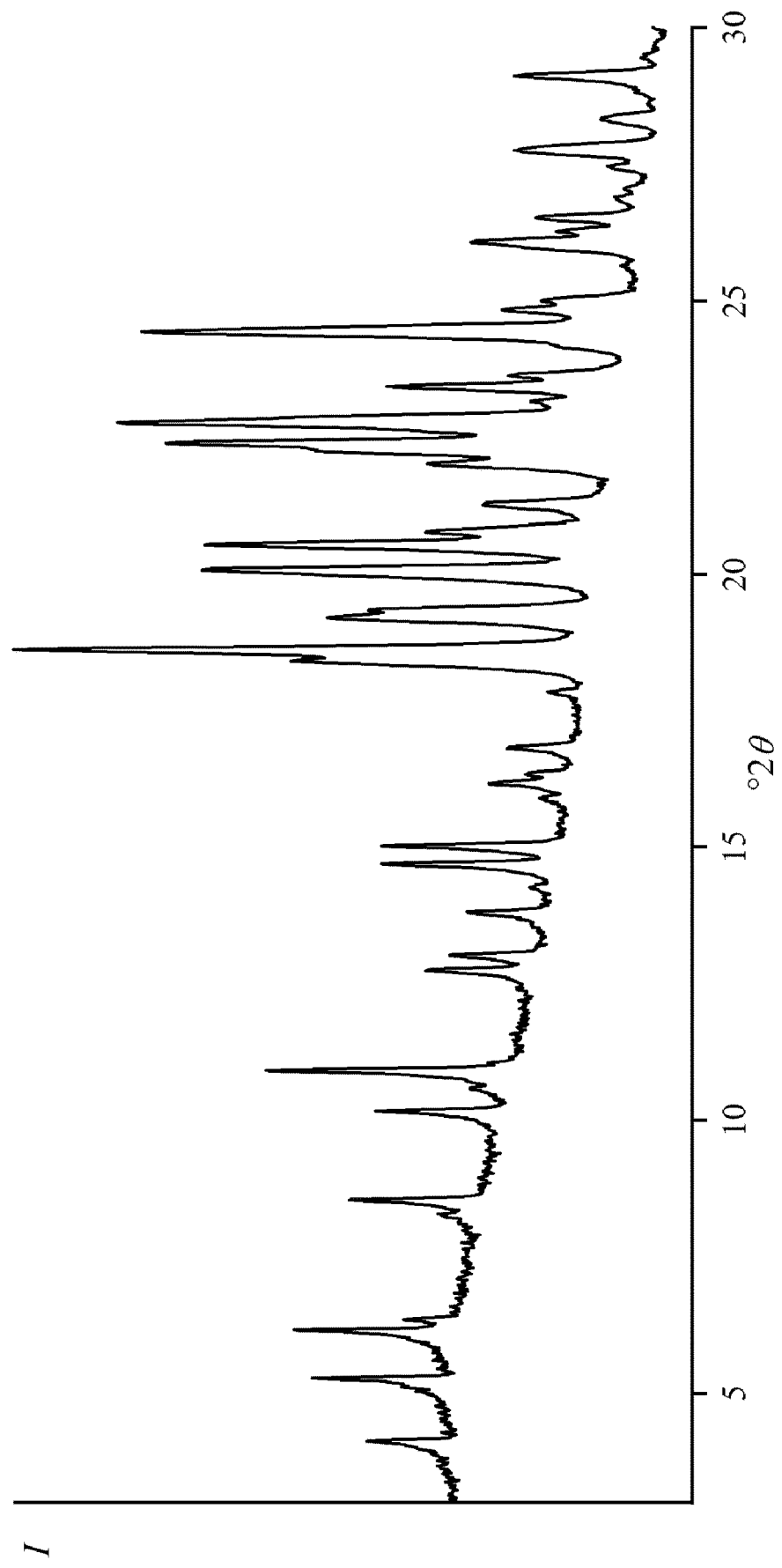
Figure 4: Powder X-ray diffraction pattern of crystalline "Form I"

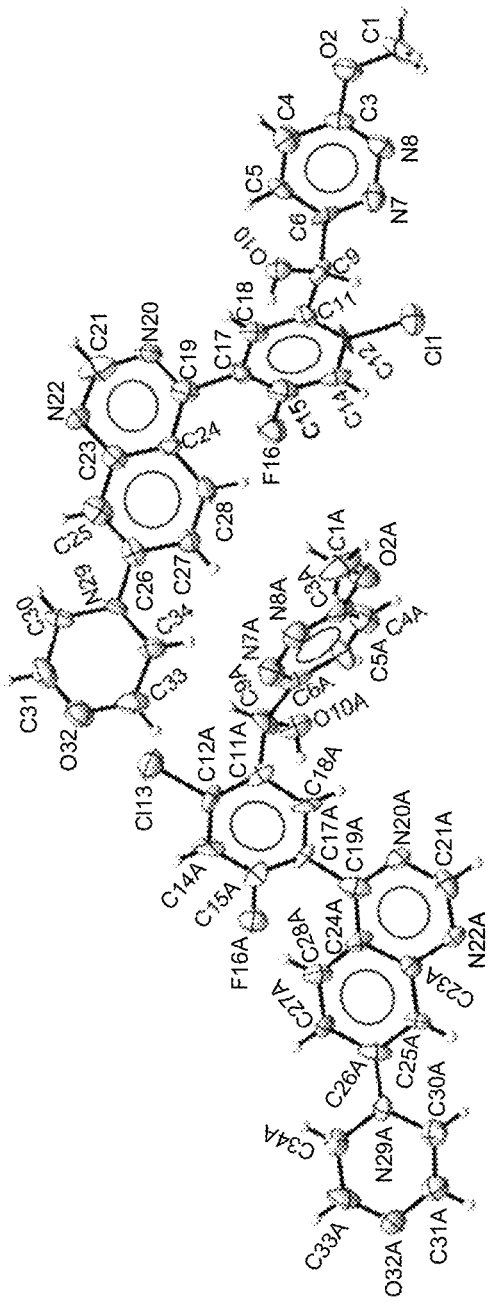
Figure 5: Crystal structure of "Form I"

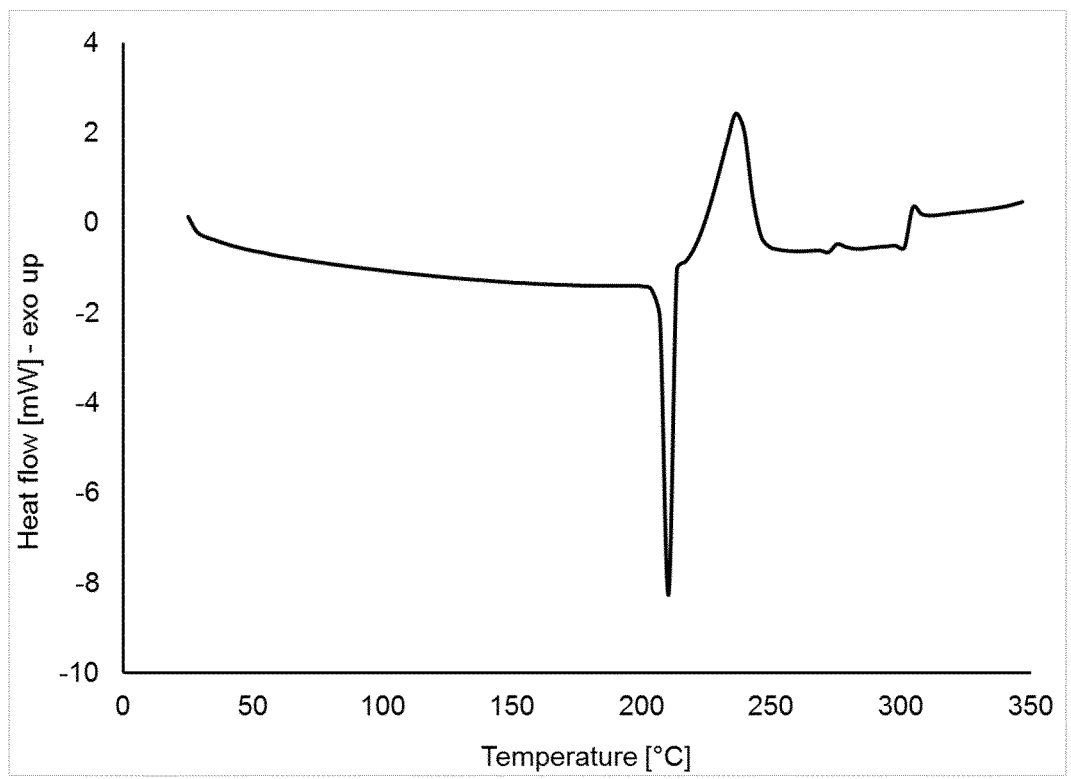
Fig. 6: DSC scan of Form I
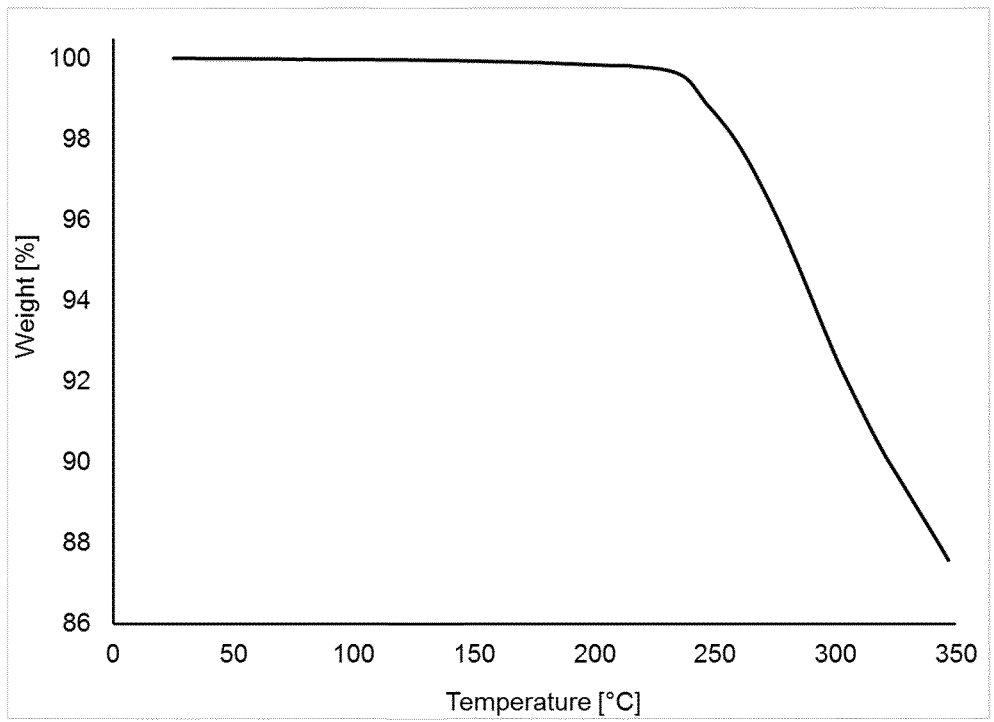
Fig. 7: TGA scan of Form I

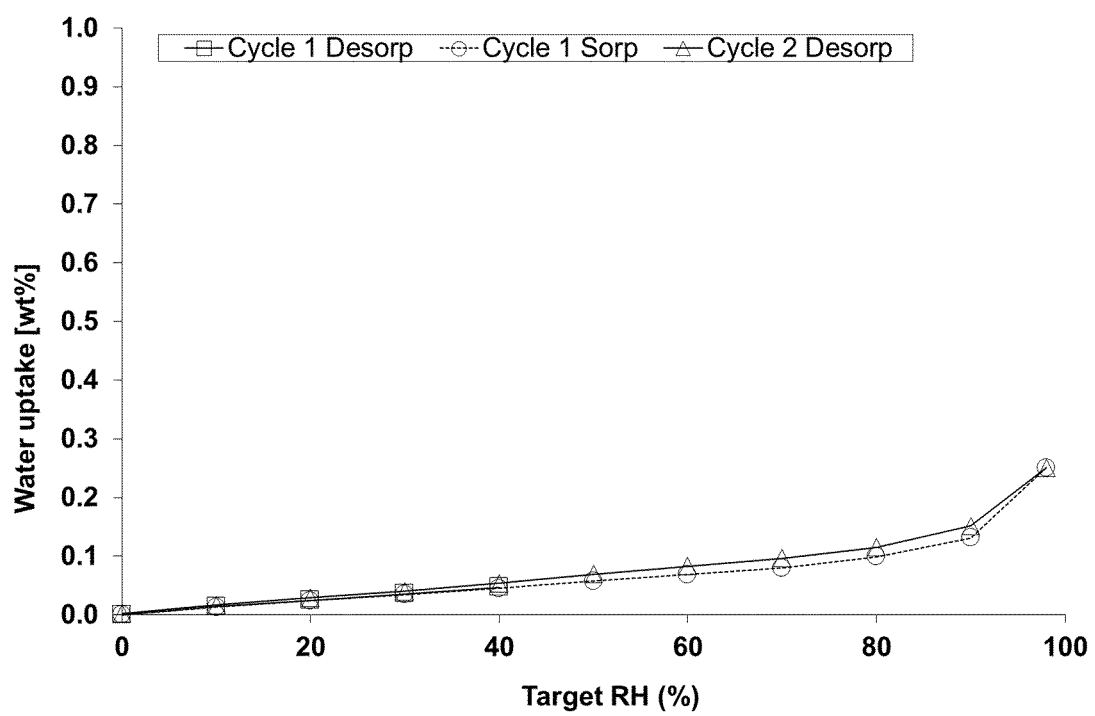
Fig. 8: Water vapour sorption isotherm of Form I

CRYSTALLINE FORM OF (S)-[2-CHLORO-4-FLUORO-5-(7-MORPHOLIN-4-YL-QUINAZOLIN-4-YL)PHENYL]-(6-METHOXY-PYRIDAZIN-3-YL)-METHANOL

CROSS-REFERENCE TO A RELATED APPLICATION

This application is a National Stage entry under § 371 of International Application No. PCT/EP2018/057869, filed on Mar. 28, 2018, and which claims the benefit of European Application No. 17163821.6, filed on Mar. 30, 2017.

BACKGROUND OF THE INVENTION

The present invention relates to a crystalline form of (S)-[2-chloro-4-fluoro-5-(7-morpholin-4-yl-quinazolin-4-yl)phenyl]-(6-methoxy-pyridazin-3-yl)-methanol, as well as a method of making same, and pharmaceutical compositions and medical uses thereof.

(S)-[2-chloro-4-fluoro-5-(7-morpholin-4-yl-quinazolin-4-yl)phenyl]-(6-methoxy-pyridazin-3-yl)-methanol, the compound depicted below, is disclosed as Example 136 in WO 2014/183850, as one member of a family of arylquinolines which have been found to have valuable pharmacological properties.

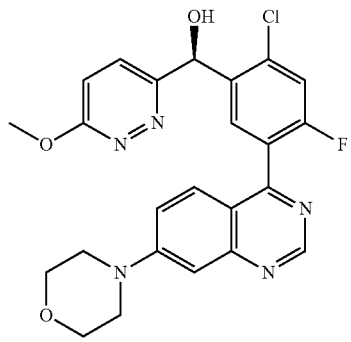 [SMILES: COc1ccc([C@@H](O)c2cc(-c3ncnc4cc(N5CCOCC5)ccc34)c(F)cc2Cl)nn1]

(S)-[2-chloro-4-fluoro-5-(7-morpholin-4-yl-quinazolin-4-yl)phenyl]-(6-methoxy-pyridazin-3-yl)-methanol is a potent and selective inhibitor of DNA-dependent protein kinase (DNA-PK) activity translating into potent inhibition of DNA-PK autophosphorylation in cancer cell lines, which has been demonstrated both by in vitro as well as in vivo data. It can therefore be used, in particular, for the sensitisation of cancer cells to anticancer agents and/or ionising radiation.

Human genetic material in the form of DNA is constantly subjected to attack by reactive oxygen species (ROSs), which are formed principally as by-products of oxidative metabolism. ROSs are capable of causing DNA damage in the form of single-strand breaks. Double-strand breaks can arise if prior single-strand breaks occur in close proximity. In addition, single- and double-strand breaks may be caused if the DNA replication fork encounters damaged base patterns. Furthermore, exogenous influences, such as ionising radiation (for example gamma or particle radiation), and certain anticancer medicaments (for example bleomycin) are capable of causing DNA double-strand breaks. DSBs may furthermore occur as intermediates of somatic recombination, a process which is important for the formation of a functional immune system of all vertebrates.

If DNA double-strand breaks are not repaired or are repaired incorrectly, mutations and/or chromosome aberrations may occur, which may consequently result in cell death. In order to counter the severe dangers resulting from DNA double-strand breaks, eukaryotic cells have developed a number of mechanisms to repair them. Higher eukaryotes use predominantly so-called non-homologous end-joining, in which the DNA-dependent protein kinase (DNA-PK) adopts the key role. DNA-dependent protein kinase (DNA-PK) is a serine/threonine protein kinase which is activated in conjunction with DNA. Biochemical investigations have shown that DNA-PK is activated most effectively by the occurrence of DNA-DSBs. Cell lines whose DNA-PK components have mutated and are non-functional have proven to be radiation-sensitive (Smith and Jackson, 1999). DSBs are considered the most lethal type of DNA damage if left unrepaired.

WO 2014/183850 discloses that the preparation of compound 136 (S)-[2-Chloro-4-fluoro-5-(7-morpholin-4-yl-quinazolin-4-yl)phenyl]-(6-methoxy-pyridazin-3-yl)-methanol free base was carried out in analogy to previous examples and indicates that chiral separation was carried out by SFC (Supercritical Fluid Chromatography), using a certain chiral setup. However, no solid form of the enantiomer is disclosed.

It was an object of the present invention to develop a form of (S)-[2-Chloro-4-fluoro-5-(7-morpholin-4-yl-quinazolin-4-yl)phenyl]-(6-methoxy-pyridazin-3-yl)-methanol having beneficial solid-state properties and a suitable process for its manufacture.

SUMMARY OF THE INVENTION

The present invention is directed to a crystalline form of (S)-[2-chloro-4-fluoro-5-(7-morpholin-4-yl-quinazolin-4-yl)phenyl]-(6-methoxy-pyridazin-3-yl)-methanol and crystalline (S)-[2-chloro-4-fluoro-5-(7-morpholin-4-yl-quinazolin-4-yl)phenyl]-(6-methoxy-pyridazin-3-yl)-methanol as such:

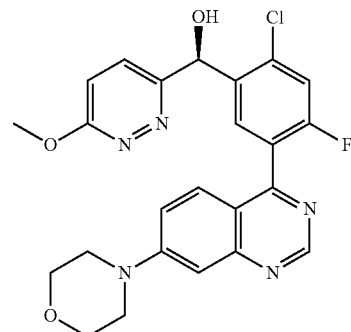

The present invention further pertains to a method of preparing crystalline (S)-[2-chloro-4-fluoro-5-(7-morpholin-4-yl-quinazolin-4-yl)phenyl]-(6-methoxy-pyridazin-3-yl)-methanol, in particular a specific crystalline form thereof, a pharmaceutical composition comprising said crystalline form, crystalline (S)-[2-chloro-4-fluoro-5-(7-morpholin-4-yl-quinazolin-4-yl)-phenyl]-(6-methoxy-pyridazin-3-yl)-methanol for use in the treatment of cancer, either alone or in combination with radiotherapy and/or chemotherapy and use of the crystalline compound in the preparation of a pharmaceutical dosage form.

The present invention further relates to the use of said crystalline form in the preparation of a pharmaceutical dosage form.

BRIEF DESCRIPTION OF THE FIGURES

FIG. 1 shows a powder X-ray diffractogram (PXRD) of amorphous (S)-[2-chloro-4-fluoro-5-(7-morpholin-4-yl-quinazolin-4-yl)phenyl]-(6-methoxy-pyridazin-3-yl)-methanol (comparative example), FIG. 4 shows a powder X-ray diffractogram (PXRD) of Form I of (S)-[2-chloro-4-fluoro-5-(7-morpholin-4-yl-quinazolin-4-yl)phenyl]-(6-methoxy-pyridazin-3-yl)-methanol, FIG. 5 depicts a schematic illustration of the crystal structure of Form I, FIG. 6 shows a DSC scan of Form I, FIG. 7 depicts a TGA profile of Form I, FIG. 8 shows the water vapour sorption isotherm of Form I.

DETAILED DESCRIPTION OF THE INVENTION

Figure 2A:
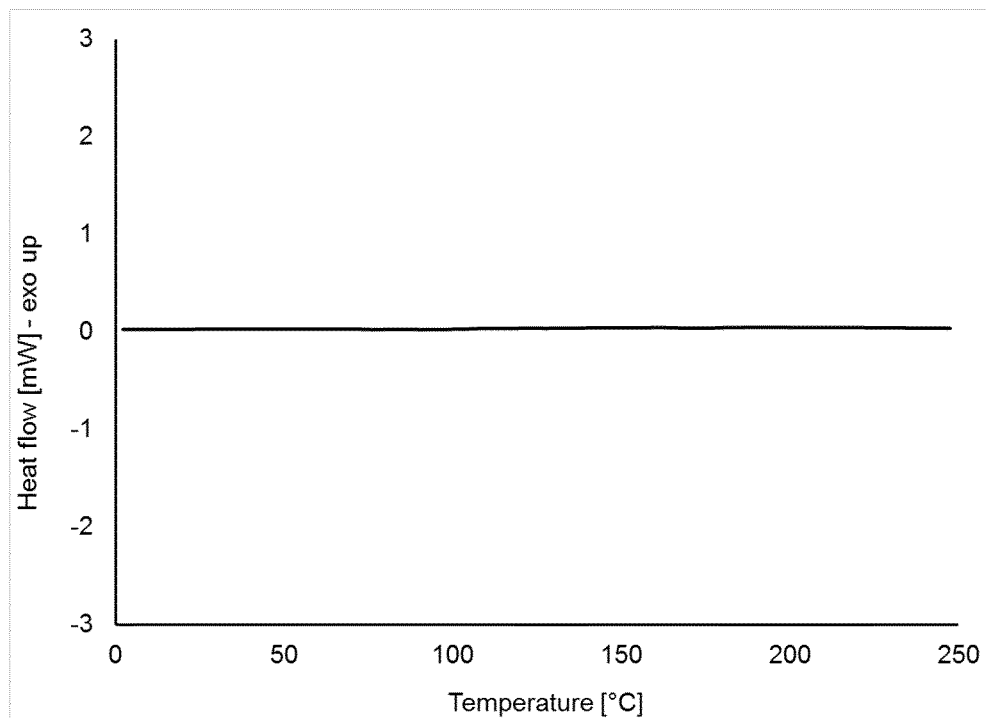
FIG. 2 shows DSC scans of amorphous (S)-[2-chloro-4-fluoro-5-(7-morpholin-4-yl-quinazolin-4-yl)phenyl]-(6-methoxy-pyridazin-3-yl)-methanol, A: reversing heat flow, B: non-reversing heat-flow (comparative example)

As explained above, the synthesis of (S)-[2-chloro-4-fluoro-5-(7-morpholin-4-yl-quinazolin-4-yl)phenyl]-(6-methoxy-pyridazin-3-yl)-methanol as such is described in WO 2014/183850, the entirety of which is disclosed by reference herein.

A solid state form of the enantiomer is not disclosed in the application. If the enantiomer is freeze-dried from a solution of acetonitrile and water, as described for the racemic mixture from which the enantiomer was separated, the entantiomer is obtained in an amorphous form, as will be described in more detail in COMPARATIVE EXAMPLE 1.

However, such an amorphous solid form of (S)-[2-Chloro-4-fluoro-5-(7-morpholin-4-yl-quinazolin-4-yl)phenyl]-(6-methoxy-pyridazin-3-yl)-methanol exhibits unfavourable particle properties. The material thus obtained is, for instance, hygroscopic, highly voluminous and electrostatically charged and thus far from ideal in terms of further processing into a solid formulation.

The present invention now provides crystalline (S)-[2-chloro-4-fluoro-5-(7-morpholin-4-yl-quinazolin-4-yl)phenyl]-(6-methoxy-pyridazin-3-yl)-methanol. More particularly, the present invention provides a novel crystalline form of S)-[2-Chloro-4-fluoro-5-(7-morpholin-4-yl-quinazolin-4-yl)phenyl]-(6-methoxy-pyridazin-3-yl)-methanol. Said novel crystalline form of (S)-[2-Chloro-4-fluoro-5-(7-morpholin-4-yl-quinazolin-4-yl)phenyl]-(6-methoxy-pyridazin-3-yl)-methanol, which is characterized as described below, has been shown to exhibit beneficial solid state properties. For ease of reference, this crystalline form may also be referred to as "Form I" in the following.

As used herein, designation of a compound as "crystalline" shall encompass both pure and substantially pure crystalline compounds, with "substantially pure crystalline" compound encompassing a compound containing less than 25%, more preferably less than 20%, more preferably less than 10% and most preferably less than 5%, less than 2.5% or less than 1% of compound that is not crystalline or, in the context of a particular polymorphic form, has a different crystalline form, i.e. a different polymorph of the compound. Expressed differently, the particular "crystalline" form is at least 75% pure with respect to other forms or other polymorphs, i.e. at least 75% of the compound are present in the particular polymorphic form. More preferably, at least 80%, e.g. at least 90%, e.g. at least 95%, most preferably at least 97.5%, e.g. at least 99% of the compound are present in the particular polymorphic form, which is Form I according to the present invention. Quantitative phase analysis can be carried out in accordance with methods known in the art (e.g. European Pharmacopeia $6^{th}$ Edition chapter 2.9.33, Section "Quantitative phase analysis").

Any reference herein to (S)-[2-chloro-4-fluoro-5-(7-morpholin-4-yl-quinazolin-4-yl)phenyl]-(6-methoxy-pyridazin-3-yl)-methanol refers to the free form of the molecule as depicted above, rather than a salt form.

Furthermore, the present invention provides anhydrous crystalline (S)-[2-chloro-4-fluoro-5-(7-morpholin-4-yl-quinazolin-4-yl)phenyl]-(6-methoxy-pyridazin-3-yl)-methanol, respectively an anhydrous crystalline form of the compound.

In particular, the present invention is concerned with a crystalline form of (S)-[2-chloro-4-fluoro-5-(7-morpholin-4-yl-quinazolin-4-yl)phenyl]-(6-methoxy-pyridazin-3-yl)-methanol, which is characterized by a powder X-ray diffraction pattern having at least two peaks at degrees two theta (°2θ) selected from 4.1, 5.2, 6.1, 8.3, 8.5, 10.1, 10.9, 12.7, 13.0, 13.8, 14.7, 15.0, 18.6, 19.2, 20.0, 20.5, 20.8, 21.3, 22.0, 22.4, 22.8, 23.4, 24.4, each ±0.2 degrees two theta, wherein at least one of the at least two peaks is selected from 4.1, 5.2, 8.3, 8.5, 10.1, 10.9, 12.7, 13.0 and 21.3 degrees two theta (°2θ), each peak ±0.2 degrees two theta. A powder X-ray diffractogram of said "Form I" is depicted in FIG. 4.

The crystalline form of (S)-[2-chloro-4-fluoro-5-(7-morpholin-4-yl-quinazolin-4-yl)phenyl]-(6-methoxy-pyridazin-3-yl)-methanol (Form I) may further be characterized as having at least three peaks, preferably four, five or six peaks in a powder X-ray diffraction pattern, at: 4.1±0.2 °2θ, 5.2±0.2 °2θ, 6.1±0.2 °2θ, 8.3±0.2 °2θ, 8.5±0.2 °2θ, 10.1±0.2 °2θ, 10.9±0.2 °2θ, 12.7±0.2 °2θ, 13.0±0.2 °2θ, 13.8±0.2 °2θ, 14.7±0.2 °2θ, 15.0±0.2 °2θ, 18.6±0.2 °2θ, 19.2±0.2 °2θ, 20.0±0.2 °2θ, 20.5±0.2 °2θ, 20.8 0.2 °2θ, 21.3 0.2 °2θ, 22.0±0.2 °2θ, 22.4±0.2 °2θ, 22.8±0.2 °2θ, 23.4±0.2 °2θ, 24.4±0.2 °2θ, wherein at least one of the peaks is selected from 4.1±0.2 °2θ, 5.2±0.2 °2θ, 8.3±0.2 °2θ, 8.5±0.2 °2θ, 10.1±0.2 °2θ, 10.9±0.2 °2θ, 12.7±0.2 °2θ, 13.0±0.2 °2θ, and 21.3±0.2 °2θ.

For instance, Form I can be characterized by a powder X-ray diffraction pattern having a peak at 4.1±0.2 °2θ, and at least one more, preferably two more, preferably three or four more peaks selected from 5.2±0.2 °2θ, 6.1 t 0.2 °2θ, 8.3±0.2 °2θ, 8.5±0.2 °2θ, 10.1±0.2 °2θ, 10.9±0.2 °2θ, 12.7±0.2 °2θ, 13.0±0.2 °2θ, 13.8±0.2 °2θ, 14.7±0.2 °2θ, 15.0±0.2 °2θ, 18.6±0.2 °2θ, 19.2±0.2 °2θ, 20.0±0.2 °2θ, 20.5±0.2 °2θ, 20.8±0.2 °2θ, 21.3±0.2 °2θ, 22.0±0.2 °2θ, 22.4±0.2 °2θ, 22.8±0.2 °2θ, 23.4±0.2 °2θ, 24.4±0.2 °2θ. In the alternative, Form I can be characterized by a powder X-ray diffraction pattern having a peak at 5.2±0.2 °2θ, and at least one more, preferably two more, preferably three or four more peaks selected from 4.1±0.2 °2θ, 6.1±0.2 °2θ, 8.3±0.2 °2θ, 8.5 0.2 °2θ, 10.1±0.2 °2θ, 10.9±0.2 °2θ, 12.7±0.2 °2θ, 13.0±0.2 °2θ, 13.8±0.2 °2θ, 14.7±0.2 °2θ, 15.0±0.2 °2θ, 18.6±0.2 °2θ, 19.2±0.2 °2θ, 20.0±0.2 °2θ, 20.5±0.2 °2θ, 20.8±0.2 °2θ, 21.3±0.2 °2θ, 22.0±0.2 °2θ, 22.4±0.2 °2θ, 22.8±0.2 °2θ, 23.4±0.2 °2θ, 24.4±0.2 °2θ. In the alternative, Form I can be characterized by a powder X-ray diffraction pattern having a peak at 5.2±0.2 °2θ, and at least one more, preferably two more, preferably three or four more peaks selected from 4.1±0.2 °2θ, 6.1±0.2 °2θ, 8.3±0.2 °2θ, 8.5±0.2 °2θ, 10.1±0.2 °2θ, 10.9±0.2 °2θ, 12.7±0.2 °2θ, 13.0±0.2 °2θ, 13.8±0.2 °2θ, 14.7±0.2 °2θ, 15.0±0.2 °2θ, 18.6±0.2 °2θ, 19.2±0.2 °2θ, 20.0±0.2 °2θ, 20.5±0.2 °2θ, 20.8±0.2 °2θ, 21.3±0.2 °2θ, 22.0±0.2 °2θ, 22.4±0.2 °2θ, 22.8±0.2 °2θ, 23.4±0.2 °2θ, 24.4±0.2 °2θ. In the alternative, Form I can be characterized by a powder X-ray diffraction pattern having a peak at 8.3±0.2 °2θ, and at least one more, preferably two more, preferably three or four more peaks selected from 4.1±0.2 °2θ, 5.2±0.2 °2θ, 6.1±0.2 °2θ, 8.5±0.2 °2θ, 10.1±0.2 °2θ, 10.9±0.2 °2θ, 12.7±0.2 °2θ, 13.0±0.2 °2θ, 13.8 t 0.2 °2θ, 14.7±0.2 °2θ, 15.0±0.2 °2θ, 18.6±0.2 °2θ, 19.2±0.2 °2θ, 20.0 t 0.2 °2θ, 20.5±0.2 °2θ, 20.8±0.2 °2θ, 21.3±0.2 °2θ, 22.0±0.2 °2θ, 22.4±0.2 °2θ, 22.8±0.2 °2θ, 23.4±0.2 °2θ, 24.4±0.2 °2θ. In the alternative, Form I can be characterized by a powder X-ray diffraction pattern having a peak at 8.5±0.2 °2θ, and at least one more, preferably two more, preferably three or four more peaks selected from 4.1±0.2 °2θ, 5.2±0.2 °2θ, 6.1±0.2 °2θ, 8.3±0.2 °2θ, 10.1±0.2 °2θ, 10.9±0.2 °2θ, 12.7±0.2 °2θ, 13.0±0.2 °2θ, 13.8±0.2 °2θ, 14.7±0.2 °2θ, 15.0±0.2 °2θ, 18.6±0.2 °2θ, 19.2±0.2 °2θ, 20.0±0.2 °2θ, 20.5±0.2 °2θ, 20.8±0.2 °2θ, 21.3±0.2 °2θ, 22.0±0.2 °2θ, 22.4±0.2 °2θ, 22.8±0.2 °2θ, 23.4±0.2 °2θ, 24.4±0.2 °2θ. In the alternative, Form I can be characterized by a powder X-ray diffraction pattern having a peak at 10.1±0.2 °2θ, and at least one more, preferably two more, preferably three or four more peaks selected from 4.1±0.2 °2θ, 5.2±0.2 °2θ, 6.1±0.2 °2θ, 8.3±0.2 °2θ, 8.5±0.2 °2θ, 10.9±0.2 °2θ, 12.7±0.2 °2θ, 13.0±0.2 °2θ, 13.8±0.2 °2θ, 14.7±0.2 °2θ, 15.0±0.2 °2θ, 18.6±0.2 °2θ, 19.2±0.2 °2θ, 20.0±0.2 °2θ, 20.5±0.2 °2θ, 20.8±0.2 °2θ, 21.3±0.2 °2θ, 22.0±0.2 °2θ, 22.4±0.2 °2θ, 22.8±0.2 °2θ, 23.4±0.2 °2θ, 24.4±0.2 °2θ. In the alternative, Form I can be characterized by a powder X-ray diffraction pattern having a peak at 10.9 0.2 °2θ, and at least one more, preferably two more, preferably three or four more peaks selected from 4.1±0.2 °2θ, 5.2±0.2 °2θ, 6.1±0.2 °2θ, 8.3±0.2 °2θ, 8.5±0.2 °2θ, 10.1±0.2 °2θ, 12.7±0.2 °2θ, 13.0±0.2 °2θ, 13.8±0.2 °2θ, 14.7±0.2 °2θ, 15.0±0.2 °2θ, 18.6±0.2 °2θ, 19.2±0.2 °2θ, 20.0±0.2 °2θ, 20.5±0.2 °2θ, 20.8 0.2 °2θ, 21.3±0.2 °2θ, 22.0±0.2 °2θ, 22.4±0.2 °2θ, 22.8±0.2 °2θ, 23.4±0.2 °2θ, 24.4±0.2 °2θ. In the alternative, Form I can be characterized by a powder X-ray diffraction pattern having a peak at 12.7±0.2 °2θ, and at least one more, preferably two more, preferably three or four more peaks selected from 4.1±0.2 °2θ, 5.2±0.2 °2θ, 6.1±0.2 °2θ, 8.3±0.2 °2θ, 8.5±0.2 °2θ, 10.1±0.2 °2θ, 10.9±0.2 °2θ, 13.0±0.2 °2θ, 13.8±0.2 °2θ, 14.7±0.2 °2θ, 15.0±0.2 °2θ, 18.6±0.2 °2θ, 19.2±0.2 °2θ, 20.0±0.2 °2θ, 20.5±0.2 °2θ, 20.8±0.2 °2θ, 21.3±0.2 °2θ, 22.0±0.2 °2θ, 22.4±0.2 °2θ, 22.8±0.2 °2θ, 23.4±0.2 °2θ, 24.4±0.2 °2θ. In the alternative, Form I can be characterized by a powder X-ray diffraction pattern having a peak at 13.0±0.2 °2θ, and at least one more, preferably two more, preferably three or four more peaks selected from 4.1±0.2 °2θ, 5.2±0.2 °2θ, 6.1±0.2 °2θ, 8.3±0.2 °2θ, 8.5±0.2 °2θ, 10.1±0.2 °2θ, 10.9±0.2 °2θ, 12.7±0.2 °2θ, 13.8±0.2 °2θ, 14.7 0.2 °2θ, 15.0±0.2 °2θ, 18.6±0.2 °2θ, 19.2±0.2 °2θ, 20.0±0.2 °2θ, 20.5±0.2 °2θ, 20.8±0.2 °2θ, 21.3±0.2 °2θ, 22.0±0.2 °2θ, 22.4±0.2 °2θ, 22.8±0.2 °2θ, 23.4±0.2 °2θ, 24.4±0.2 °2θ. In a further alternative, Form I can be characterized by a powder X-ray diffraction pattern having a peak at 21.3±0.2 °2θ, and at least one more, preferably two more, preferably three or four more peaks selected from 4.1±0.2 °2θ, 5.2±0.2 °2θ, 6.1±0.2 °2θ, 8.3±0.2 °2θ, 8.5±0.2 °2θ, 10.1±0.2 °2θ, 10.9±0.2 °2θ, 12.7±0.2 °2θ, 13.0±0.2 °2θ, 13.8±0.2 °2θ, 14.7±0.2 °2θ, 15.0±0.2 °2θ, 18.6±0.2 °2θ, 19.2±0.2 °2θ, 20.0±0.2 °2θ, 20.5±0.2 °2θ, 20.8±0.2 °2θ, 22.0±0.2 °2θ, 22.4±0.2 °2θ, 22.8±0.2 °2θ, 23.4±0.2 °2θ, 24.4±0.2 °2θ.

Expressed differently, Form I can be characterized by a powder X-ray diffraction pattern having several, preferably three, four or most preferably five or six peaks are selected from 4.1±0.2 °2θ, 5.2±0.2 °2θ, 6.1±0.2 °2θ, 8.3±0.2 °2θ, 8.5±0.2 °2θ, 10.1±0.2 °2θ, 10.9±0.2 °2θ, 12.7±0.2 °2θ, 13.0±0.2 °2θ, 13.8±0.2 °2θ, 14.7±0.2 °2θ, 15.0±0.2 °2θ, 18.6±0.2 °2θ, 19.2±0.2 °2θ, 20.0±0.2 °2θ, 20.5±0.2 °2θ, 20.8±0.2 °2θ, 21.3±0.2 °2θ, 22.0±0.2 °2θ, 22.4±0.2 °2θ, 22.8±0.2 °2θ, 23.4±0.2 °2θ, 24.4±0.2 °2θ, of which at least two peaks, more preferably three peaks or four peaks are selected from 4.1±0.2 °2θ, 5.2±0.2 °2θ, 8.3±0.2 °2θ, 8.5±0.2 °2θ, 10.1±0.2 °2θ, 10.9±0.2 °2θ, 12.7±0.2 °2θ. 13.0±0.2 °2θ, and 21.3±0.2 °2θ.

Preferably, the peaks characterizing Form I are one ore more of: 4.1±0.1 °2θ, 5.2±0.1 °2θ, 6.1±0.1 °2θ, 8.3±0.1 °2θ, 8.5±0.1 °2θ, 10.1±0.1 °2θ, 10.9±0.1 °2θ, 12.7±0.1 °2θ, 13.0±0.1 °2θ, 13.8±0.1 °2θ, 14.7±0.1 °2θ, 15.0±0.1 °2θ, 18.6±0.1 °2θ, 19.2±0.1 °2θ, 20.0±0.1 °2θ, 20.5 0.1 °2θ, 20.8±0.1 °2θ, 21.3±0.1 °2θ, 22.0±0.1 °2θ, 22.4±0.1 °2θ, 22.8±0.1 °2θ, 23.4±0.1 °2θ, 24.4±0.1 °2θ, wherein at least one peak, for instance one, two or three peaks is/are selected from 4.1±0.1 °2θ, 5.2±0.1 °2θ, 8.3±0.1 °2θ, 8.5±0.1 °2θ, 10.1±0.1 °2θ, 10.9±0.1 °2θ, 12.7±0.1 °2θ, 13.0±0.1 °2θ, 14.7±0.1 °2θ, 19.2±0.1 °2θ, and 21.3±0.1 °2.

The powder X-ray diffraction pattern peaks referred to above are those recorded on the basis of Cu-Kai radiation (λ=1.54 Å). Generally, powder X-ray diffraction patterns can be obtained by standard techniques known in the art, such as described in the European Pharmacopeia 6$^{th}$ Edition chapter 2.9.33. Further details regarding the powder X-ray diffraction method that has been employed in the recording of the powder X-ray diffraction pattern peaks forming the basis for the above values will be described further below.

The term "peak" is used herein in accordance with its established meaning in the art and synonymously with the term "maximum".

In a further aspect, the crystalline form of (S)-[2-chloro-4-fluoro-5-(7-morpholin-4-yl-quinazolin-4-yl)phenyl]-(6-methoxy-pyridazin-3-yl)-methanol according to the present invention, in particular the crystalline "Form I" as described and characterized above, is anhydrous.

The crystalline form of (S)-[2-chloro-4-fluoro-5-(7-morpholin-4-yl-quinazolin-4-yl)phenyl]-(6-methoxy-pyridazin-3-yl)-methanol according to the invention (Form I), may of course, be characterized by an powder X-ray diffraction pattern substantially in accordance with FIG. 4.

The powder X-ray diffraction patterns depicted in FIGS. 1 and 4 were obtained by standard techniques as described in the European Pharmacopeia 6th Edition chapter 2.9.33, for instance, as will be set out in more experimental detail below. As will be understood by the person skilled in the art, relative intensities (intensity I) in such diffraction patterns may vary to a relatively large extent, for instance up to 20 percent. Thus, a diffraction pattern would be "substantially in accordance" with that in FIG. 4, if there is a peak within an experimental error of about ±0.2 °2θ at the indicated diffraction angle.

The following Table 1 sets out a list of X-ray peaks of crystalline Form I:

TABLE 1

| List of X-ray peaks of crystalline Form I | |
|---|---|
| Peak No. | °2θ (Cu-Kα$_1$ radiation) ± 0.2° |
| 1 | 4.1 |
| 2 | 5.2 |

TABLE 1-continued

List of X-ray peaks of crystalline Form I

| Peak No. | °2θ (Cu-Kα$_1$ radiation) ± 0.2° |
|---|---|
| 3 | 6.1 |
| 4 | 8.3 |
| 5 | 8.5 |
| 6 | 10.1 |
| 7 | 10.9 |
| 8 | 12.7 |
| 9 | 13.0 |
| 10 | 13.8 |
| 11 | 14.7 |
| 12 | 15.0 |
| 13 | 18.6 |
| 14 | 19.2 |
| 15 | 20.0 |
| 16 | 20.5 |
| 17 | 20.8 |
| 18 | 21.3 |
| 19 | 22.0 |
| 20 | 22.4 |
| 21 | 22.8 |
| 22 | 23.4 |
| 23 | 24.4 |

By way of comparison, the X-ray diffraction "pattern" of amorphous (S)-[2-chloro-4-fluoro-5-(7-morpholin-4-yl-quinazolin-4-yl)phenyl]-(6-methoxy-pyridazin-3-yl)-methanol as prepared in accordance with Comparative Example 1, is shown in FIG. 1. As expected for amorphous material, it only shows a broad background hump, with the exception of a peak at about 5.5 °2θ, which is an artefact in the measurement.

It is further noted that the diffraction pattern of crystalline Form I illustrates an ordered crystalline lattice, as evident from the sharp peaks. Thus, any peak selected from 4.1, 5.2, 6.1, 8.3, 8.5, 10.1, 10.9, 12.7, 13.0, 13.8, 14.7, 15.0, 18.6, 19.2, 20.0, 20.5, 20.8, 21.3, 22.0, 22.4, 22.8, 23.4, and/or 24.4, each ±0.2 degrees two theta, may optionally be individually characterized as having full width at half maximum (FWHM) of less than 0.2 °2θ.

Crystalline form I crystallises in the orthorhombic space group P2$_1$2$_1$2$_1$ with the lattice parameters a=4.8 Å, b=27.5 Å, c=33.3 Å and α=β=γ=90°. The form may be further characterized in that there are 8 formula units per unit cell and the unit cell volume is 4436 Å3. The crystalline form may further be described by a calculated density of 1.44 g/cm$^3$. These data were generated based upon single crystal X-ray structure data using a Rigaku SuperNova diffractometer, equipped with CCD detector using Cu-Kα radiation at 200 K.

The crystal structure of Form I is illustrated in FIG. 5.

The crystalline form of the compound has favourable solid state properties. In particular, it lacks the voluminous nature and electrostatic charge of the amorphous material. It is also advantageous with respect to thermal and water uptake behaviour, as explained in more detail below.

Figure 2B:
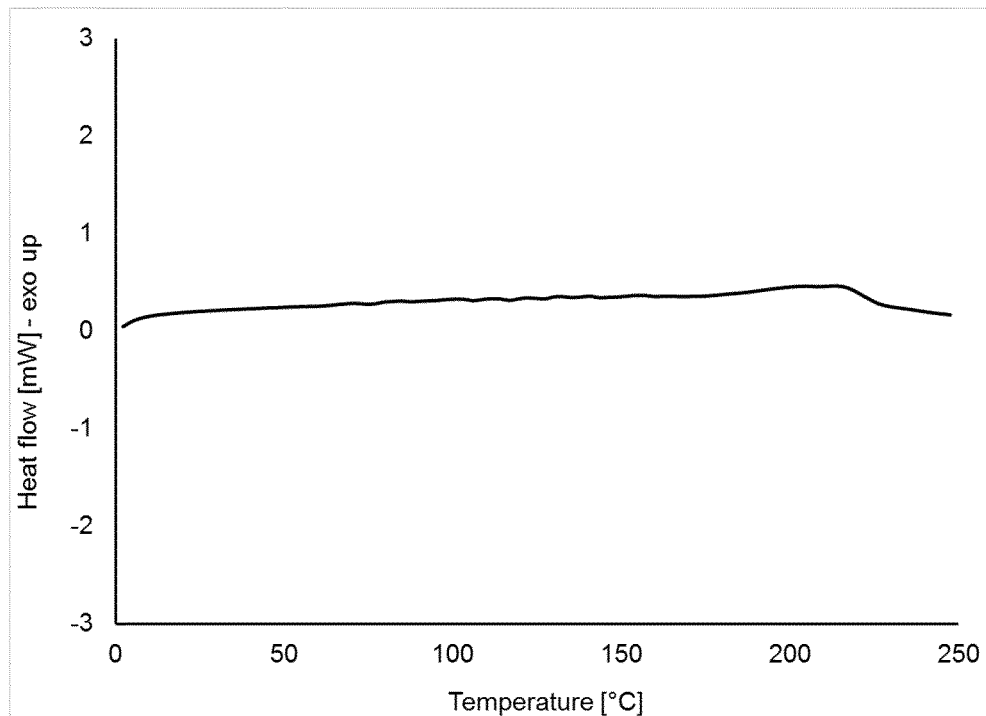

In terms of thermal behaviour, Form I shows no thermal events prior to melting/decomposition above 200° C., as apparent from DSC and TGA profiles as depicted in FIGS. 6 and 7. By contrast, the amorphous material decomposes at 170° C. (FIG. 2). The crystalline material therefore lends itself to further processing that involves high temperatures, such as hot melt extrusion and melt granulation.

Figure 3:
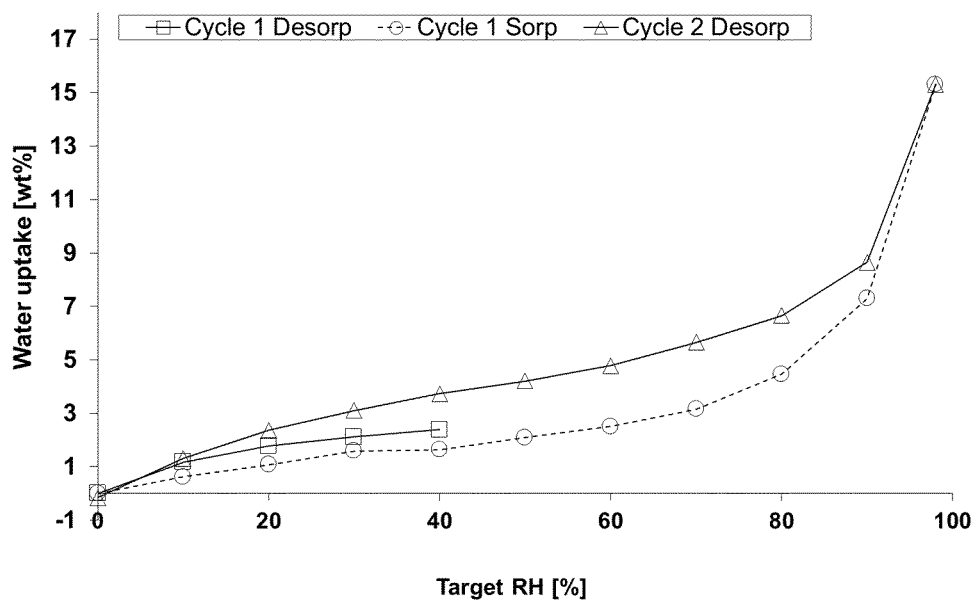
FIG. 3 shows the water vapour sorption isotherm of amorphous (S)-[2-chloro-4-fluoro-5-(7-morpholin-4-yl-quinazolin-4-yl)phenyl]-(6-methoxy-pyridazin-3-yl)-methanol (comparative example)

The Water Vapour Sorption behaviour shows only very small water uptake levels <1% m/m in the relative humidity (rh) range 40-80% rh. Form I can therefore be classified acc. to Ph. Eur. Criteria (section 5.11.) as not hygroscopic. The max. water uptake level ($\Delta m_{max}$ at 98% rh) of Form I is <1% m/m. The water Vapor Sorption isotherm (25° C.) of Form I is displayed in FIG. 8. In contrast, the amorphous material shows significant water uptake (FIG. 3). This non-hygroscopic behaviour of Form I is advantageous both in case of using the material as a starting material, as it readily lends itself to storage, as well as using it "as is" in a pharmaceutical dosage form.

The crystalline (S)-[2-chloro-4-fluoro-5-(7-morpholin-4-yl-quinazolin-4-yl)-phenyl]-(6-methoxy-pyridazin-3-yl)-methanol according to the present invention, in particular crystalline "Form I", has solubility characteristics that render it suitable also for biorelevant intestinal media. The crystalline (S[2-chloro-4-fluoro-5-(7-morpholin-4-yl-quinazolin-4-yl)phenyl]-(6-methoxy-pyridazin-3-yl)-methanol can be characterized by one or more of the following:

| Medium | pH of medium | Solubility [μg/ml] | T [° C.] |
|---|---|---|---|
| SGF | 1.2 | 891 ± 33 | 37 |
| FaSSIF | 6.5 | 3 ± 0 | 37 |
| FeSSIF | 5.0 | 17 ± 1 | 37 |

Solubility measurements were carried out in accordance with the method(s) described further below.

It is noted that anhydrous crystalline Form I is particularly advantageous not only with respect to amorphous material, but also with respect to other crystalline forms that could principally be prepared. Other obtainable forms, include, for instance, a further anhydrous form, which crystallizes in the monoclinic space group C2 with the lattice parameters a=29.26 Å, b=4.96 Å, c=19.2 Å and α=γ=90° and β=127.14°, and which may be further characterized in that there are 4 formula units per unit cell and the unit cell volume is 2221 Å$^3$. Said form can be obtained by cooling crystallisation from pure 1,4-dioxane and is metastable. A further obtainable crystalline form is a 1,4-dioxane solvate, which can be prepared by organic vapour sorption involving 1,4-dioxane/water, and is characterized by a monoclinic space group C2 with the lattice parameters a=28.67 Å, b=5.09 Å, c=20.86 Å and α=γ=90° and β=114.18°, and which is further characterized in that there are 4 formula units per unit cell and the unit cell volume is 2779 Å$^3$. However, said solvate is unsuitable for pharmaceutical purposes.

The present invention further pertains to a process for preparing crystalline (S)-[2-chloro-4-fluoro-5-(7-morpholin-4-yl-quinazolin-4-yl)phenyl]-(6-methoxy-pyridazin-3-yl)-methanol, most preferably anhydrous crystalline S)-[2-chloro-4-fluoro-5-(7-morpholin-4-yl-quinazolin-4-yl)phenyl]-(6-methoxy-pyridazin-3-yl)-methanol, comprising a) preparing a clear solution of (S)-[2-chloro-4-fluoro-5-(7-morpholin-4-yl-quinazolin-4-yl)phenyl]-(6-methoxy-pyridazin-3-yl)-methanol in a solvent or solvent mixture, optionally with heating, b) cooling the clear solution, c) separating the crystalline (S)-[2-chloro-4-fluoro-5-(7-morpholin-4-yl-quinazolin-4-yl)phenyl]-(6-methoxy-pyridazin-3-yl)-methanol from the solvent or solvent mixture, and d) drying the crystalline (S)-[2-chloro-4-fluoro-5-(7-morpholin-4-yl-quinazolin-4-yl)phenyl]-(6-methoxy-pyridazin-3-yl)-methanol.

In preferred embodiments, the above process is a process for preparing an anhydrous crystalline form of of (S)-[2- chloro-4-fluoro-5-(7-morpholin-4-yl-quinazolin-4-yl)phenyl]-(6-methoxy-pyridazin-3-yl)-methanol, in particular Form I, i.e. the crystalline form of (S)-[2-chloro-4-fluoro-5-(7-morpholin-4-yl-quinazolin-4-yl)phenyl]-(6-methoxy-pyridazin-3-yl)-methanol as characterized above. In particular, the process for preparing said crystalline form (Form I) may comprise:

a) preparing a clear solution of (S)-[2-chloro-4-fluoro-5-(7-morpholin-4-yl-quinazolin-4-yl)phenyl]-(6-methoxy-pyridazin-3-yl)-methanol in a solvent or solvent mixture, optionally with heating, b) cooling the solution at a rate which is sufficiently low to allow formation of the crystalline form, c) separating the crystalline (S)-[2-chloro-4-fluoro-5-(7-morpholin-4-yl-quinazolin-4-yl)phenyl]-(6-methoxy-pyridazin-3-yl)-methanol from the solvent or solvent mixture, and d) drying the crystalline (S)-[2-chloro-4-fluoro-5-(7-morpholin-4-yl-quinazolin-4-yl)phenyl]-(6-methoxy-pyridazin-3-yl)-methanol to produce Form I.

In the process according to the invention, the solvent or solvent mixture may be chosen, for instance, from methanol, ethanol, 1-propanol, acetone, methyl ethyl ketone, methyl isobutyl ketone, ethyl acetate, tetrahydrofurane, acetonitrile, and mixtures of two or more of these, and in particular mixtures of water/1,4-dioxane, water/pyridine, methanol/tetrahydrofurane, methanol/chloroform, methanol/N,N-dimethylformamide, methanol/pyridine, 2-propanol/tetrahydrofurane, 2-propanol/pyridine, acetone/1,4-dioxane, acetone/chloroform, acetone/N,N-dimethylformamide, and acetone/pyridine.

Specific suitable solvent mixtures include, in particular, for instance, water/1,4-dioxane (1:1 v:v), water/pyridine (1:0.4 v:v), methano/tetrahydrofurane (1:0.4 v:v), methanol/chloroform (1:0.2 v:v), methanol/N,N-dimethylformamide (1:0.3 v:v), methanol/pyridine (1:02 v:v), 2-propanol/tetrahydrofurane (1:0.7 v:v), 2-propanol/pyridine (1:0.4 v:v)), acetone/1,4-dioxane (1:0.6 v:v), acetone/chloroform (1:1.2 v:v), acetone/N,N-dimethylformamide (1:0.2 v:v) and acetone/pyridine (1:0.2 v:v).

Any reference to water is to be understood as referring to deionised distilled water. The abbreviation v:v stands for volume per volume, as customary in the art (m:m accordingly for mass per mass).

For instance, the cooling rate in step b) may be 1 K/min or less, such as 0.2 K/min or less, for instance 0.15 K/min or less, such as 0.05 K/min or less.

Step a) of the process according to the present invention is preferably carried out with heating, for instance with heating to 40° C. or more, for instance 45° C. or more, more preferably 50° C. or more. This applies, in particular to the above mentioned solvents and solvent mixtures. In case of an ethanol/water mixture, heating is preferably to 70° C. or more, for instance 75° C. or more, more preferably 80° C. or more.

Preparation of the clear solution may include filtering the solvent or solvent mixture containing the (S)-[2-chloro-4-fluoro-5-(7-morpholin-4-yl-quinazolin-4-yl)phenyl]-(6-methoxy-pyridazin-3-yl)-methanol. It may in the alternative comprise concentrating the solution, for instance by way of evaporation.

Step b) of the process according to the present invention may involve cooling and stirring the solution. Cooling of the solution may be, for instance, to a temperature of 25° C. or less, for instance 20° C. or less, for instance 15° C. or less, for instance 10° C. or less or 5° C. or less.

The separating step c) may be effected by filtration or centrifugation, to name but two examples.

Drying of the crystalline compound according to step d) of the process may be under reduced pressure, such as under vacuum, for instance, or under inert gas, such as nitrogen, in particular dry nitrogen. Furthermore, drying may be at room temperature or at elevated temperature, for instance at at least 40° C. or more, for instance 50° C. or more, for instance 60° C. or more, or 70° C. or more. The drying conditions are generally chosen in dependence of the solvent/solvent mixture used in the preparation of the crystalline material, as will be further exemplified with reference to the exemplary embodiments described in detail below.

Accordingly, the present invention further pertains to crystalline (S)-[2-chloro-4-fluoro-5-(7-morpholin-4-yl-quinazolin-4-yl)phenyl]-(6-methoxy-pyridazin-3-yl)-methanol, which is obtainable according to the process described above.

In a further aspect, the present invention provides a pharmaceutical formulation comprising crystalline (S)-[2-chloro-4-fluoro-5-(7-morpholin-4-yl-quinazolin-4-yl)phenyl]-(6-methoxy-pyridazin-3-yl)-methanol, in particular Form I thereof, optionally and preferably in combination with one or more pharmaceutically acceptable excipients.

Preferably, the pharmaceutical dosage form is for oral administration. Pharmaceutical dosage forms may comprise any dosage form wherein the material is contained in the crystalline form, including in particular solid dosage forms, such as capsules, tablets, lozenges, pills, powders, granules or ointments or sprays. Typically, the pharmaceutical dosage forms comprise one or more excipients.

In one aspect, the pharmaceutical dosage form is a tablet and comprises the crystalline compound, in particular Form I thereof, as well as one or more excipients selected, for instance, from: a) a filler, b) a binder, c) a humectant, d) a disintegrating agent, e) a wicking agent, f) a matrix former, and g) a lubricant. Suitable excipients are known in the art.

The present invention further pertains to the use of crystalline (S)-[2-chloro-4-fluoro-5-(7-morpholin-4-yl-quinazolin-4-yl)phenyl]-(6-methoxy-pyridazin-3-yl)-methanol according to the invention, in particular Form I, in the preparation of a pharmaceutical dosage form, wherein the preparation may involve dissolving or dispersing the crystalline (S)-[2-chloro-4-fluoro-5-(7-morpholin-4-yl-quinazolin-4-yl)phenyl]-(6-methoxy-pyridazin-3-yl)-methanol in a melting or molten polymer.

Accordingly, the invention is further directed to using the crystalline (S)-[2-chloro-4-fluoro-5-(7-morpholin-4-yl-quinazolin-4-yl)phenyl]-(6-methoxy-pyridazin-3-yl)-methanol according to the invention, in particular Form I, in the preparation of a pharmaceutical dosage form, involving melt granulation or hot melt extrusion of (S)-[2-chloro-4-fluoro-5-(7-morpholin-4-yl-quinazolin-4-yl)phenyl]-(6-methoxy-pyridazin-3-yl)-methanol and a polymer to produce a solid dispersion of (S)-[2-chloro-4-fluoro-5-(7-morpholin-4-yl-quinazolin-4-yl)phenyl]-(6-methoxy-pyridazin-3-yl)-methanol.

The invention further relates to a method of preparing a pharmaceutical formulation comprising (S)-[2-chloro-4-fluoro-5-(7-morpholin-4-yl-quinazolin-4-yl)phenyl]-(6-methoxy-pyridazin-3-yl)-methanol, comprising a step of using the Form I thereof for melt granulation or hot melt extrusion in combination with a polymer to produce a solid dispersion of (S)-[2-chloro-4-fluoro-5-(7-morpholin-4-yl-quinazolin-4-yl)phenyl]-(6-methoxy-pyridazin-3-yl)-methanol.

Accordingly, the present invention further relates to the crystalline (S)-[2-chloro-4-fluoro-5-(7-morpholin-4-yl-quinazolin-4-yl)phenyl]-(6-methoxy-pyridazin-3-yl)-methanol according to the invention, in particular Form I, preferably in the form of a pharmaceutical dosage form as referred to above, for use in the treatment of cancer.

In some embodiments, the cancer treatment further comprises at least one of radiotherapy and chemotherapy. For instance, the crystalline compound, in particular Form I according to the invention, may be advantageously used in combination with radiotherapy. In other embodiments, the cancer treatment further comprises chemotherapy, i.e. administration of at least one other anticancer agent. For instance, the other anticancer agent may be selected from cisplatin and carboplatin. In still further embodiments, the cancer treatment comprises both radiotherapy and chemotherapy, for instance administration of cisplatin or carboplatin and radiotherapy.

Accordingly, the present invention provides a method of treating a patient in need thereof, comprising administering a pharmaceutical formulation comprising crystalline (S)-[2-chloro-4-fluoro-5-(7-morpholin-4-yl-quinazolin-4-yl)phenyl]-(6-methoxy-pyridazin-3-yl)-methanol according to the invention, in particular Form I, to the patient. In analogy to what has been disclosed above, treating the patient may further comprise at least one of treatment by radiotherapy and chemotherapy.

Analytical Methods:

Powder X-ray diffractions (XRPD) were obtained by standard techniques as described in the European Pharmacopeia 7$^{th}$ Edition chapter 2.9.33 (Cu-Kai radiation, λ=1.5406 Å, Stoe StadiP 611 KL transmission diffractometer, ambient temperature); and in particular For the amorphous form: The XRPD measurement was performed in transmission geometry with Cu-K$_{\alpha 1}$ radiation on a Stoe StadiP 611 diffractometer equipped with Mythen1K Si-strip detector (PSD). Approximately 5-20 mg of the sample were prepared on a combinatorial 96-well-plate sample holder comprising a mostly amorphous Kapton® foil on the bottom of the wells. Measurement was carried out by setting following parameters:
angular range: −36°–36 °2θ folded to 0-36 °2θ
angular resolution: 0.03 °2θ
PSD step with: 4 °2θ
measurement time: 30 s/PSD-step
generator settings: 40 mA, 40 kV For the crystalline Form I: The measurement was performed in transmission geometry with Cu-K$_{\alpha 1}$ radiation on a Stoe StadiP 611 diffractometer equipped with Mythen1K Si-strip detector (PSD). Approximately 10-100 mg of the sample were prepared between amorphous films. Measurement was carried out by setting following parameters:
angular range: 1°–41 °2θ
angular resolution: 0.015 °2θ
PSD step with: 0.49 °2θ
measurement time: 15 s/PSD-step
generator settings: 40 mA, 40 kV

DSC:

For the amorphous form:

Temperature modulated DSC (TOPEM®) was acquired on a Mettler-Toledo heat-flux Differential Scanning Calorimeter DSC 1 system. Approximately 0.5 mg sample amount were weighed accurately in a 40 μl Aluminium pan which was hermetically closed by a lid. The scan was carried out from 0° C. to 250° C. with a linear heating rate of 2 K/min, overlapped by a non-linear puls-modulated temperature programme with a pulse height of ±0.5 K and a stochastic pulse width from 15 s (min) to 45 s (max). Nitrogen purge gas at 50 mL/min was used.

For crystalline Form I:

DSC measurement was acquired on Mettler-Toledo heat-flux Differential Scanning Calorimeter system DSC 821e. Approximately 1-5 mg sample amount were weighed accurately in a 40 μl Aluminium pan with pierced lid. The scan was carried out from 25° C. to 350° C. with a linear heating rate of 5 K/min and a nitrogen purge gas at 50 mL/min.

TGA:

Sample was investigated on a Mettler-Toledo Thermogravimetric Analyser TGA 851 with autosampler, using a nitrogen inert gas atmosphere (flow 50 mL/min). Approximately 5-20 mg sample amount were weighed accurately in a 100 μl Aluminium pan and hermetically closed by Aluminium lids. Just before insertion to the oven the lid was pierced by a needle of the autosampler system. Scans were carried out from 25° C. to 350° C. at 5 K/min. The result was baseline-corrected with a blank run from an empty 100 μl Aluminium pan of the same type, using the identical temperature profile.

Water Vapour Sorption Isotherm:

Approximately 1-40 mg sample amount were weighed accurately into a 100 μl Al pan and hung into the sample position of the DVS instrument with microbalance and incubator (DVS-Intrinsic; Surface Measurement Systems, SMS). A nitrogen overall follow rate of 200 ml/min (combined dry and humid stream) was used for controlled humidification. A Water vapour sorption isotherm was acquired at 25° C., using following desorption-sorption-desorption cycles:
initial desorption: 40% rh to 0% rh (10% rh steps)
sorption: 0% rh to 98% rh (10% rh steps and a final 8% rh step)
second desorption: 98% rh to 0% rh (with an initial 8% rh step and consecutive 10% rh steps)

(rh stands for relative humidity)

For all rh steps, an equilibrium condition of dm/dt≤0.0005 wt %/min was used, with a minimum rh step time of 10 minutes and a maximum rh step time (timeout) of 360 minutes.

According to Ph. Eur., hygroscopicity of solid API powders is classified based on the Water uptake at 80% rh (compared to Water uptake at ambient conditions). Assuming that 40% rh can be considered as lowest rh level to be expected for ambient conditions, the following threshold levels can be defined:
dm (80% rh–40% rh)<0.2 wt %: not hygroscopic
0.2 wt %≤dm (80% rh–40% rh)<2.0 wt %: slightly hygroscopic
2.0 wt %≤dm (80% rh–40% rh)<15.0 wt %: hygroscopic
15.0 wt %≤dm (80% rh–40% rh): very hygroscopic Solubility Measurements:

Test Media:

SGF (Simulated gastric fluid without pepsin) pH 1.2: 2.0 g sodium chloride were placed in a 1 L volumetric flask and dissolved in around 500 mL water. 80 mL of 1 M hydrochloric acid solution were added and the volume made up to 1 L.

The resulting SGF solution contains: 34.2 mM sodium chloride

FaSSIF (Fasted State Simulated Intestinal Fluid) pH 6.5:
0.224 g SIF Powder (obtained from biorelevant.com) were dissolved in FaSSIF buffer in a 100 mL volumetric flask and made up to volume. The FaSSIF medium was allowed to equilibrate for 2 h at ambient room temperature and used within 48 h of preparation. FaSSIF buffer can be made up by dissolving 0.42 g NaOH pellets, 3.44 g of monobasic sodium phosphate anhydrous and 6.19 g sodium chloride in about 0.9 L of purified water, adjusting the pH to 6.5 with 1 N NaOH or 1 N HCl and making up the volume to 1 L.
The resulting FaSSIF contains: 3 mM sodium taurocholate; 0.75 mM lecithin; 105.9 mM sodium chloride; 28.4 mM monobasic sodium phosphate and 8.7 mM sodium hydroxide.
FeSSIF (Fed State Simulated Intestinal Fluid) pH 5.0:
1.12 g SIF powder (biorelevant.com) were dissolved in FeSSIF buffer in a 100 mL volumetric flask and made up to volume. It was used within 48 h of preparation. FeSSIF buffer can be made up by dissolving 4.04 g NaOH pellets, 8.65 g of glacial acetic acid and 11.87 g sodium chloride in about 0.9 L of purified water, adjusting the pH to 6.5 with 1 N NaOH or 1 N HCl and making up the volume to 1 L. The resulting FeSSIF contains: 15 mM sodium taurocholate; 3.75 mM lecithin; 203.2 mM sodium chloride; 101.0 mM sodium hydroxide and 144.1 mM acetic acid.
Solubility measurements: Excess amount of substance was weighed into Uniprep® Whatman vials, to which 1 mL of test medium were added. The suspension was shaken for 24 h at 450 rpm (rounds per minute) at 37° C. The pH was measured at 1 h, 6 h and 24 h and the vials were checked for undissolved compound. The pH of the medium was adjusted wherever necessary. After 24 h, the solutions were filtered through 0.2 μm PTFE membrane filter and the filtrates analysed using HPLC after suitable dilutions.
HPLC:
Apparatus: Agilent 1100
Column: Chromolith® Performance RP-18e100-3 mm, Art. 1.52001 (h)
Wavelength: 282 nm
Injection volume: 5 μL
Column Oven: 37° C.
Auto sampler: 37° C.
Eluent A for HPLC: Formic Acid: Ultrapure water (1:999; v/v)
Eluent B for HPLC: Formic Acid+Acetonitrile (1:999; v/v)
HPLC-Gradient:

| Time (minutes) | Eluent A (%) | Eluent B (%) | Flow (mL/min) |
|---|---|---|---|
| 0.00 | 90 | 10 | 1.70 |
| 0.30 | 90 | 10 | 1.70 |
| 2.00 | 10 | 90 | 1.70 |
| 2.75 | 10 | 90 | 1.70 |
| 2.76 | 90 | 10 | 2.50 |
| 4.00 | 90 | 10 | 2.50 |

$^1$H NMR:
The NMR measurements were performed on a Bruker AV500 spectrometer equipped with a TCI cryocooled probehead.

Approximately 5-20 mg of the sample were dissolved in 0.7 ml DMSO-de. The $^1$H-NMR experiments were run at 500 MHz proton resonance frequency and 303 Kelvin.

The invention will now be described with regard to exemplary embodiments of the present invention, which shall not be regarded as limiting the invention, and comparative example. As used herein, "substance" or "compound" refers to (S)-[2-chloro-4-fluoro-5-(7-morpholin-4-yl-quinazolin-4-yl)phenyl]-(6-methoxy-pyridazin-3-yl-methanol.

Comparative Example 1: Preparation of Amorphous Material by Lyophilisation 14 mg substance were dissolved in 90 mL acetonitrile/Water, 1:3 (v/v) at RT. The obtained solution was filtered through a 0.45 μm syringe filter into a 250 mL round bottom flask to remove foreign particles. The clear solution was quenched by plunge in liquid nitrogen. The frozen solvent mixture was completely removed by lyophilisation under vacuum (approx. 0.04 mbar).

Example 1

4.7 kg crude substance was added to a stirred solution of ethanol/water, 9:1 (v/v) at reflux (IT=78° C.) until a clear solution was obtained (108.1 Liter). Afterwards a temperature ramp was set from 80° C. to 10° C. over 8 hours (approx. 0.146 K/min). The obtained crystallisate was stirred over night at 10° C. The solid-/liquid-separation was done by filtration and the solid material was dried under vacuum at 70° C.

$^1$H NMR (500 MHz, DMSO-d6) δ 9.12 (s, 1H), 7.92 (d, J=7.8 Hz, 1H), 7.70 (d, J=9.2 Hz, 1H), 7.67 (d, J=9.5 Hz, 1H), 7.59 (dd, J=9.4, 3.4 Hz, 1H), 7.54 (dd, J=9.5, 2.5 Hz, 1H), 7.24-7.19 (m, 2H), 6.64 (d, J=4.9 Hz, 1H), 6.23 (d, J=4.9 Hz, 1H), 4.00 (s, 3H), 3.82-3.69 (m, 4H), 3.48-3.39 (m, 4H)

Example 2

480 g substance were dissolved in 6 L dichloromethane/methanol, 5:1 and filtered. The filtrate was concentrated in rotary evaporator. The residue was re-crystallised in 3 L acetone. The obtained solid material was suspended in 4 L acetone and stirred i h at 50° C. After cooling to 25° C. the yellow solid material was filtered and dried for 24 h at 40° C. in the vacuum-compartment dryer.

Example 3

Approx. 20 mg substance were dissolved or suspended in several solvents (see Table 2 below) at 50° C. The solutions/suspensions were filtered through 0.2 μm syringe filters. The obtained clear solutions were cooled down to 5° C. with a ramp of approx. 0.05 K/min. While cooling the solutions were stirred with PTFE coated stirring bars by a magnetic stirrer. The solid-/liquid-separations of obtained suspensions were done by centrifugation and the solid materials were dried overnight at room temperature with a dry nitrogen flow. The solvents used in these experiments are compiled in Table 2 below.

TABLE 2

| Solvent/solvent mixture | Volume [mL] |
| --- | --- |
| Methanol | 4 |
| Ethanol | 4 |
| 1-Propanol | 4 |
| Acetone | 4 |
| Methyl ethyl ketone | 4 |
| Methyl isobutyl ketone | 4 |
| Ethyl acetate | 4 |
| Tetrahydrofuran | 1 |
| Acetonitrile | 4 |
| H$_2$O/1,4-Dioxane, 1:1 (v:v) | 2 |
| H$_2$O/Pyridine, 1:0.4 (v:v) | 1.4 |
| Methanol/Tetrahydrofuran, 1:0.4 (v:v) | 1.4 |
| Methanol/Chloroform, 1:0.2 (v:v) | 1.2 |
| Methanol/N,N-Dimethylformamide, 1:0.3 (v:v) | 1.3 |
| Methanol/Pyridine, 1:0.2 (v:v) | 1.2 |
| 2-Propanol/Tetrahydrofuran, 1:0.7 (v:v) | 1.7 |
| 2-Propanol/N,N-Dimethylformamide, 1:0.5 (v:v) | 1.5 |
| 2-Propanol/Pyridine, 1:0.4 (v:v) | 1.4 |
| Acetone/1,4-Dioxane, 1:0.6 (v:v) | 1.6 |
| Acetone/Tetrahydrofuran, 1:0.7 (v:v) | 1.7 |
| Acetone/Chloroform, 1:1.2 (v:v) | 2.2 |
| Acetone/N,N-Dimethylformamide, 1:0.2 (v:v) | 1.2 |
| Acetone/Pyridine, 1:0.2 (v:v) | 1.2 |

The invention claimed is:

1. A crystalline form of (S)-[2-chloro-4-fluoro-5-(7-morpholin-4-yl-quinazolin-4-yl)-phenyl]-(6-methoxy-pyridazin-3-yl)-methanol.

2. A crystalline form of (S)-[2-chloro-4-fluoro-5-(7-morpholin-4-yl-quinazolin-4-yl)-phenyl]-(6-methoxy-pyridazin-3-yl)-methanol, which is characterized by a powder X-ray diffraction pattern having at least two peaks at degrees two theta selected from the group consisting of 4.1, 5.2, 6.1, 8.3, 8.5, 10.1, 10.9, 12.7, 13.0, 13.8, 14.7, 15.0, 18.6, 19.2, 20.0, 20.5, 20.8, 21.3, 22.0, 22.4, 22.8, 23.4, and 24.4, each ±0.2 degrees two theta.

3. The crystalline form of (S)-[2-chloro-4-fluoro-5-(7-morpholin-4-yl-quinazolin-4-yl)-phenyl]-(6-methoxy-pyridazin-3-yl)-methanol according to claim 2, which is characterized by a powder X-ray diffraction pattern having at least three peaks at degrees two theta selected from the group consisting of 4.1, 5.2, 6.1, 8.3, 8.5, 10.1, 10.9, 12.7, 13.0, 13.8, 14.7, 15.0, 18.6, 19.2, 20.0, 20.5, 20.8, 21.3, 22.0, 22.4, 22.8, 23.4, and 24.4, each ±0.2 degrees two theta.

4. The crystalline form of (S)-[2-chloro-4-fluoro-5-(7-morpholin-4-yl-quinazolin-4-yl)-phenyl]-(6-methoxy-pyridazin-3-yl)-methanol according to claim 1, which is an anhydrate.

5. The crystalline form of (S)-[2-chloro-4-fluoro-5-(7-morpholin-4-yl-quinazolin-4-yl)-phenyl]-(6-methoxy-pyridazin-3-yl)-methanol according to claim 1, which is characterized by a powder X-ray diffraction pattern substantially in accordance with FIG. 4.

6. The crystalline form of (S)-[2-chloro-4-fluoro-5-(7-morpholin-4-yl-quinazolin-4-yl)-phenyl]-(6-methoxy-pyridazin-3-yl)-methanol according to claim 1, which has a solubility in a simulated gastric fluid without pepsin at a pH of 1.2 of more than 850 µg/mL.

7. A process for preparing the crystalline form of (S)-[2-chloro-4-fluoro-5-(7-morpholin-4-yl-quinazolin-4-yl)-phenyl]-(6-methoxy-pyridazin-3-yl)-methanol according to claim 1, comprising:
   a) preparing a clear solution of (S)-[2-chloro-4-fluoro-5-(7-morpholin-4-yl-quinazolin-4-yl)-phenyl]-(6-methoxy-pyridazin-3-yl)-methanol in a solvent or solvent mixture, optionally with heating,
   b) cooling the clear solution,
   c) separating the crystalline form of (S)-[2-chloro-4-fluoro-5-(7-morpholin-4-yl-quinazolin-4-yl)-phenyl]-(6-methoxy-pyridazin-3-yl)-methanol from the solvent or solvent mixture, and
   d) drying the crystalline form of (S)-[2-chloro-4-fluoro-5-(7-morpholin-4-yl-quinazolin-4-yl)-phenyl]-(6-methoxy-pyridazin-3-yl)-methanol.

8. The process according to claim 7, wherein the crystalline form of (S)-[2-chloro-4-fluoro-5-(7-morpholin-4-yl-quinazolin-4-yl)-phenyl]-(6-methoxy-pyridazin-3-yl)-methanol is characterized by a powder X-ray diffraction pattern having at least two peaks at degrees two theta selected from the group consisting of 4.1, 5.2, 6.1, 8.3, 8.5, 10.1, 10.9, 12.7, 13.0, 13.8, 14.7, 15.0, 18.6, 19.2, 20.0, 20.5, 20.8, 21.3, 22.0, 22.4, 22.8, 23.4, and 24.4, each ±0.2 degrees two theta.

9. The process according to claim 7, wherein the solvent or solvent mixture is selected from the group consisting of methanol, ethanol, 1-propanol, acetone, methyl ethyl ketone, methyl isobutyl ketone, ethyl acetate, tetrahydrofuran, acetonitrile, and mixtures of these, water/1,4-dioxane, water/pyridine, methanol/tetrahydrofuran, methanol/chloroform, methanol/N,N-dimethylformamide, methanol/pyridine, 2-propanol/tetrahydrofuran, 2-propanol/pyridine, acetone/1,4-dioxane, acetone/chloroform, acetone/ N,N-dimethylformamide, and acetone/pyridine.

10. A pharmaceutical formulation, comprising:
   the crystalline form of (S)-[2-chloro-4-fluoro-5-(7-morpholin-4-yl-quinazolin-4-yl)-phenyl]-(6-methoxy-pyridazin-3-yl)-methanol according to claim 2.

11. A method for the preparation of a pharmaceutical dosage form, comprising:
   mixing the crystalline form of (S)-[2-chloro-4-fluoro-5-(7-morpholin-4-yl-quinazolin-4-yl)-phenyl]-(6-methoxy-pyridazin-3-yl)-methanol according to claim 2 with one or more pharmaceutically acceptable excipients.

12. A method for the preparation of a pharmaceutical dosage form of the crystalline form of (S)-[2-chloro-4-fluoro-5-(7-morpholin-4-yl-quinazolin-4-yl)-phenyl]-(6-methoxy-pyridazin-3-yl)-methanol according to claim 2, the method comprising:
   dissolving or dispersing the crystalline (S)-[2-chloro-4-fluoro-5-(7-morpholin-4-yl-quinazolin-4-yl)-phenyl]-(6-methoxy-pyridazin-3-yl)-methanol in a melting polymer or molten polymer.

13. The method according to claim 12, further comprising:
   hot melt extruding or hot melt granulating of (S)-[2-chloro-4-fluoro-5-(7-morpholin-4-yl-quinazolin-4-yl)-phenyl]-(6-methoxy-pyridazin-3-yl)-methanol and a polymer to produce a solid dispersion of (S)-[2-chloro-4-fluoro-5-(7-morpholin-4-yl-quinazolin-4-yl)-phenyl]-(6-methoxy-pyridazin-3-yl)-methanol in the polymer.

14. A method of preparing a pharmaceutical formulation comprising (S)-[2-chloro-4-fluoro-5-(7-morpholin-4-yl-quinazolin-4-yl)-phenyl]-(6-methoxy-pyridazin-3-yl)-methanol, comprising:
   hot melt extruding or hot melt granulating of the crystalline form of (S)-[2-chloro-4-fluoro-5-(7-morpholin-4-yl-quinazolin-4-yl)-phenyl]-(6-methoxy-pyridazin-3-yl)-methanol according to claim 2 in combination with a polymer to produce a solid dispersion of (S)-[2- chloro-4-fluoro-5-(7-morpholin-4-yl-quinazolin-4-yl)-phenyl]-(6-methoxy-pyridazin-3-yl)-methanol in the polymer.

15. A method for inhibiting DNA-dependent protein kinase (DNA-PK) in a cancer that expresses DNA-PK, comprising:
administering the crystalline form of (S)-[2-chloro-4-fluoro-5-(7-morpholin-4-yl-quinazolin-4-yl)-phenyl]-(6-methoxy-pyridazin-3-yl)-methanol according to claim 2 to a patient in need thereof, optionally in combination with at least one of radiotherapy and chemotherapy.

16. The crystalline form of (S)-[2-chloro-4-fluoro-5-(7-morpholin-4-yl-quinazolin-4-yl)-phenyl]-(6-methoxy-pyridazin-3-yl)-methanol according to claim 2, wherein the powder X-ray diffraction pattern has at least four peaks at degrees two theta selected from the group consisting of 4.1, 5.2, 6.1, 8.3, 8.5, 10.1, 10.9, 12.7, 13.0, 13.8, 14.7, 15.0, 18.6, 19.2, 20.0, 20.5, 20.8, 21.3, 22.0, 22.4, 22.8, 23.4, and 24.4, each ±0.2 degrees two theta.

17. The crystalline form of (S)-[2-chloro-4-fluoro-5-(7-morpholin-4-yl-quinazolin-4-yl)-phenyl]-(6-methoxy-pyridazin-3-yl)-methanol according to claim 2, wherein the powder X-ray diffraction pattern has at least one of the at least two peaks at degrees two theta selected from the group consisting of 4.1, 5.2, 8.3, 8.5, 10.1, 10.9, 12.7, 13.0, and 21.3, each ±0.2 degrees two theta.

18. The crystalline form of (S)-[2-chloro-4-fluoro-5-(7-morpholin-4-yl-quinazolin-4-yl)-phenyl]-(6-methoxy-pyridazin-3-yl)-methanol according to claim 1, wherein the crystalline form has a water uptake level of less than 1% m/m.

19. The method according to claim 11, wherein the at least one pharmaceutically acceptable excipient is selected from the group consisting of a filler, a binder, a humectant, a disintegrating agent, a wicking agent, a matrix former, and a lubricant.

* * * * *